United States Patent [19]
Janssens et al.

[11] Patent Number: 4,855,211
[45] Date of Patent: Aug. 8, 1989

[54] POLYMERIC PHOSPHONIUM MORDANT AND PHOTOGRAPHIC ELEMENT CONTAINING THE SAME

[75] Inventors: Wilhelmus Janssens, Aarschot; Daniël M. Timmerman; Daniël A. Claeys, both of Mortsel, all of Belgium

[73] Assignee: Agfa-Gevaert, N.V., Mortsel, Belgium

[21] Appl. No.: 228,173

[22] Filed: Aug. 4, 1988

[30] Foreign Application Priority Data

Sep. 11, 1987 [EP] European Pat. Off. ........ 87201741.3

[51] Int. Cl.$^4$ ..................... G03C 5/54; C08F 30/02; C08F 19/24; C08F 12/08
[52] U.S. Cl. .................................... 430/213; 430/941; 525/329.2; 525/333.4; 525/340; 525/333.3; 525/916; 526/274; 526/278
[58] Field of Search ............. 430/213, 941, 518; 526/274, 278; 525/329.2, 333.4, 340, 333.3, 916

[56] References Cited

U.S. PATENT DOCUMENTS

| | | | |
|---|---|---|---|
| 3,547,649 | 12/1970 | Franco | 430/941 |
| 3,958,995 | 5/1976 | Campbell et al. | 430/941 |
| 4,701,400 | 10/1987 | Katoh | 430/941 |

*Primary Examiner*—Richard L. Schilling
*Attorney, Agent, or Firm*—A. W. Breiner

[57] ABSTRACT

Phosphonium mordanting polymer, that is capable of fixing acid dyes and that comprises randomly distributed recurring units corresponding to the general formula (I)

$$\mathrm{(CH_2-CH)}_{\overline{x}} \; \mathrm{-(A)}_{\overline{y}} \; \mathrm{-(B)}_{\overline{z}} \qquad (I)$$

with a phenyl group bearing $(CH_2)_n - P^+ R_1 R_2 R_3 \; X^-$ wherein:
A represents a unit that is derived from a copolymerizable monomer capable of quenching singlet oxygen e.g. N-vinylimidazole or 2-methyl-1-vinylimidazole;
B represents a unit that is derived from a copolymerizable monomer having a hydrophobic character e.g. acrylonitrile or methacrylonitrile;
n represents an integer of from 1 to about 12;
each of $R_1$, $R_2$ and $R_3$ (same or different) represents a $C_1$–$C_8$ alkyl group e.g. n-butyl, a substituted $C_1$–$C_8$ alkyl group e.g. a methylol group, a cyanoethyl group or an aralkyl group, a cycloalkyl group, an aryl group e.g. phenyl, or a substituted aryl group;
$X^-$ represents an acid anion e.g. a halogen anion e.g. $Cl^-$, $Br^-$ or $I^-$, or an anion derived from an inorganic acid e.g. $NO_3^{31}$, $HSO_4^-$, $SO_4^{--}$, $H_2PO_4^-$, $HPO_4^{--}$ or $PO_4^{---}$;
x represents from about 5 mole % to about 80 mole %;
y represents from about 20 mole % to about 95 mole % and
z represents from about 0 mole % to about 65 mole %.

12 Claims, No Drawings

POLYMERIC PHOSPHONIUM MORDANT AND PHOTOGRAPHIC ELEMENT CONTAINING THE SAME

DESCRIPTION

The present invention relates to a polymeric phosphonium mordanting agent and to an image-receptor element, suitable for carrying out a dye diffusion transfer imaging process, containing an image-receiving layer comprising said mordanting agent.

A dye diffusion transfer process is based on the imagewise transfer of diffusible dye molecules from an imagewise exposed light-sensitive element into a water-permeable image-receiving layer containing a mordant for the dye(s). The imagewise diffusion of the dye(s) is controlled by the development of one or more imagewise exposed light-sensitive layers, that for the production of a multicolor image are differently spectrally sensitized and contain respectively yellow, magenta and cyan dye or dye-providing molecules.

The dye(s) can be made to diffuse in imagewise distribution according to any known dye diffusion transfer imaging system. All dye diffusion transfer imaging systems are based on the same principle of modifying the solubility of the dyes as a function of the amount of photographic silver halide developed. In commonly known dye diffusion transfer imaging processes the dye-providing substances are either initially mobile in alkaline aqueous media and become imagewise immobilized during processing, or initially immobile and become imagewise mobilized during processing. A survey of such processes has been given by Van de Sande C. C. in Angew. Chem. Int. Ed. Engl. 22(3), 1983, pages 191 to 209. More details on such processes and on dye-providing substances can be found in the literature cited therein and in DE-A-1095115, 1930215, 1772929, 2242762, 2505248, 2543902, 2645656, and in EP-A-89069, 109701, 173361 and 219892 and in Research Disclosure item 15162 (November 1976).

The image-receiving layer can be coated on a support and form part of a light-insensitive image-receptor element that is to be brought in contact for development with a light-sensitive element comprising a support, at least one light-sensitive silver halide emulsion layer and associated with said silver halide emulsion layer a dye-providing substance. Alternatively, such image-receiving layer can also be an integrating constituent of a monosheet material comprising a light-sensitive element and an image-receptor element.

The selection of the particular mordanting agent for mordanting or otherwise fixing the diffusing dye(s) is determined by the nature of the dye(s) to be mordanted. It is for instance known to mordant acid dyes with cationic phosphonium polymers. Unfortunately, the stability under the influence of light and ultraviolet radiation of dyes mordanted with these phosphonium polymers is insufficient.

It is an object of the present invention to provide novel mordanting phosphonium copolymers that are capable of efficiently preventing the resulting mordanted dyes from fading under the influence of light and UV-radiation.

It is another object of the present invention to provide an image-receptor element containing an image-receiving layer comprising said mordanting agent.

According to the present invention a phosphonium mordanting polymer is provided, that is capable of fixing acid dyes and that comprises randomly distributed recurring units corresponding to the general formula (I)

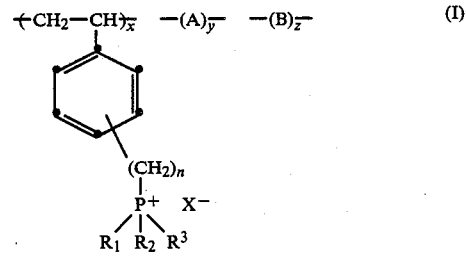

wherein:

A represents a unit that is derived from a copolymerizable monomer capable of quenching singlet oxygen e.g. N-vinylimidazole, 2-methyl-1-vinylimidazole, 2-vinylimidazoline, vinylpurine and derivatives thereof, vinylpyrimidine and derivatives thereof, 2-vinyl-3,4,5,6-tetrahydropyrimidinine, vinylamine, 1-methylvinylamine, 1-ethylvinylamine, aminoethyl acrylate, aminoethyl methacrylate, aminoethyl acrylamide, aminoethyl methacrylamide, vinylalkylamine, vinyldialkylamine, 1-methylvinylalkylamine, 1-methylvinyldialkylamine, 1-ethylvinylalkylamine, 1-ethylvinyldialkylamine, alkylaminoethyl acrylate, dialkylaminoethyl acrylate, alkylaminoethyl methacrylate or dialkylaminoethyl methacrylate with alkyl being a methyl or ethyl group;

B represents a unit that is derived from a copolymerizable monomer having a hydrophobic character e.g. styrene, vinyl toluene and homologues, 2- and 4-homologues of vinylpyridine, 2-methyl,5-vinylpyridine, alkyl methacrylate with alkyl being a $C_1$–$C_5$ alkyl group, alkyl acrylates with alkyl being a $C_1$–$C_5$ alkyl group, vinyl acetate, acrylonitrile, methacrylonitrile, allylcyanide, crotononitrile, cyanoalkyl acrylate with alkyl being a $C_1$–$C_5$ alkyl group, diacetone acrylamide or diacetone methacrylamide;

n represents an integer of from 1 to about 12;

each of $R_1$, $R_2$ and $R_3$ (same or different) represents a $C_1$–$C_8$ alkyl group e.g. n-butyl, a substituted $C_1$–$C_8$ alkyl group e.g. a methylol group, a cyanoethyl group or an aralkyl group, a cycloalkyl group, an aryl group e.g. phenyl, or a substituted aryl group;

$X^-$ represents an acid anion e.g. a halogen anion e.g. $Cl^-$, $Br^-$ or $I^-$, or an anion derived from an inorganic acid e.g. $NO_3^-$, $HSO_4^-$, $SO_4^{--}$, $H_2PO_4^-$, $HPO_4^{--}$ or $PO_4^{---}$;

X represents from about 5 mole % to about 80 mole %;

y represents from about 20 mole % to about 95 mole % and z represents from 0 mole % to about 65 mole %.

Preferred units A are N-vinylimidazole and 2-methyl-1-vinylimidazole. Preferred units B are acrylonitrile and methacrylonitrile.

The following preparations illustrate the synthesis of some particularly useful mordanting polymers in accordance with the present invention.

PREPARATION 1

Preparation of
co(N-vinylimidazole/m,p-vinylbenzyl,tributylphosphonium chloride)

(a) Preparation of
m,p-vinylbenzyl,tributylphosphonium chloride

A 3-liter reaction vessel was provided with a stirring device, a thermometer, a reflux condenser and a dropping funnel.

The following ingredients were introduced in this reaction vessel: 457.5 g (3.0 mole) of m,p-vinylbenzyl chloride (sold by Dow Chemical Co.), 1.2 g of methoxyphenol as polymerization inhibitor and 1000 ml of ethanol. The reaction mixture was stirred at room temperature to reach a homogeneous solution. This solution was placed on a water bath of 80° C.

The dropping funnel was filled with 669.8 g (3.15 mole) of 95% tributylphosphine. As soon as the solution temperature reached 38° C. one started to add the tributylphosphine at a rate of ca. 8 g/min.

The quaternization reaction proceeded exothermally and after 20 minutes the solution temperature had increased to 78° C. A gentle reflux was obtained and the heating was turned off.

After 1 h 20 min the total amount of tributylphosphine had been added and the solution temperature had dropped to 74° C. The reaction still proceeded slightly exothermally and the temperature remained constant without further heating.

After 2 h 50 min the heating was used again. The temperature in the alcohol solution increased to 78° C. whereupon it decreased slowly to 75° C. while continuously keeping the water-bath at 80° C.

After a total reaction time of 5 hours the water-bath was taken away and the solution was concentrated under reduced pressure to obtain 1234.4 g of concentrated solution.

The m,p-vinylbenzyl,tributylphosphinium chloride partially precipitated and 2100 ml of ethyl acetate was added. By heating on a water-bath of 75° C. a homogeneous solution was obtained which was filtered warm and then cooled.

The precipitated m,p-vinylbenzyl,tributylphosphonium chloride was filtered off and washed with 400 ml of ether. The filtrate was concentrated half under reduced pressure and poured out into a mixture of 1 l of hexane and 2 l of ether. A further amount of m,p-vinylbenzyl,tributylphosphonium chloride was filtered off after cooling.

Yield: 962.4 g.

By NMR analysis it was found that the obtained compound comprised at the most a few percentages of impurities. By titration it was found that the ionic chlorine content was 2.81 meq./g (99.6%) and the water content 0.42 meq./g (0.43%).

(b) Preparation of
co(N-vinylimidazole/m,p-vinylbenzyl,tributylphosphonium chloride)

In a 500 ml reaction flask, provided with stirrer, reflux condenser, thermometer and nitrogen inlet tube 25.44 g of distilled N-vinylimidazole (0.87 mole), 42.54 g of m,p-vinylbenzyl,tributylphosphonium chloride (0.12 mole) and 0.34 g of azobisisobutyronitrile together with 203 ml of ethanol were dissolved at room temperature.

A gentle nitrogen stream was introduced into this solution and the heating was switched on.

After 1 hour the solution temperature reached 78° C. and was kept constant while stirring and introducing nitrogen.

After 19 hours the solution became slightly viscous and a further amount of azobisisobutyronitrile (0.34 g) was added.

After a reaction period of 27 hours again azobisisobutyronitrile (0.20 g) was added. Hereupon the reaction mixture was stirred at 77°–78° C. under nitrogen atmosphere for 16 hours.

The polymer solution was cooled and poured out in a stirred mixture of 2 l of hexane and 1 l of acetone. The copolymer precipitated as a viscous mass, which after washing with a mixture of 200 ml of hexane and 100 ml of acetone, was redissolved again in a mixture of 400 ml of ethanol and 200 ml of water.

From a little amount of this solution the solvent was evaporated and the obtained copolymer analyzed: phosphonium chloride content=1.659 meq./g, N-vinylimidazole content: 3.957 meq./g, water content=2.15 meq./g from which can be calculated that $x=29.4$ mole % or 61.1 wt %, $y=70.6$ mole % or 38.9 wt %.

From the remaining water-alcohol solution the ethanol was removed by distillation and the pH adjusted to 7.0 by adding acetic acid. The obtained copolymer solution was diluted with water to obtain 330 g (20 wt %).

PREPARATION 2

In an anologous way as described in preparation 1, a N-vinylimidazole/m,p-vinylbenzyl,tributylphosphonium chloride copolymer was prepared starting with 33.0 g of distilled N-vinylimidazole, 31.1 g of m,p-vinylbenzyl,tributylphosphonium chloride, 200 ml of ethanol and 0.33 g of azobisisobutyronitrile. After 18 hours a further amount of azobisisobutyronitrile (0.32 g) was added and after a reaction time of 24 hours again 0.16 g azobisisobutyronitrile was added.

Yield: 65.7 g of copolymer.

Analysis of the copolymer: phosphonium chloride content=1.368 meq./g, N-vinylimidazole content=4.972 meq./g, water content=2.65 meq./g from which can be calculated that $x=21.6$ mole % or 50.9 wt %, $y=78.4$ mole % or 49.1 wt %.

PREPARATION 3

Preparation of
co(acrylonitrile/N-vinylimidazole/m,p-vinylbenzyl,-tributylphosphonium chloride)

In a 5-liter flask, provided with stirrer, reflux condenser, thermometer and nitrogen inlet tube, 148.4 g (40 mole %) of acrylonitrile, 263.2 g (40 mole %) of distilled N-vinylimidazole and 496.3 g (20 mole %) of m,p-vinylbenzyl,tributylphosphonium chloride together with 4.53 g of azobisisobutyronitrile were introduced and dissolved in 2270 ml of ethanol.

While stirring and introducing nitrogen this solution was gradually heated to obtain a gentle reflux.

At the start of the heating the solution was green colored. After 45 minutes, at a temperature of 64° C., it became deep-blue. After 1 h 30 min the temperature reached 78° C. and a gentle reflux was obtained. After 1 h 50 min the solution turned red.

After 20 hours the obtained red solution became slightly viscous and a further amount of azobisisobutyronitrile (4.53 g) was added. The color changed from red to pale-orange.

After 23 hours a relative viscous, orange-colored solution was obtained wherefrom part of the ethanol was distilled off. After 25 hours 1 l of ethanol was distilled off whereupon the viscous solution was poured out into 8 l of hexane while stirring. The precipitated copolymer was redissolved in ethanol.

Yield: 2301 g, 38.17 wt %.

Analysis of the copolymer: phosphonium chloride content=1.439 meq./g, N-vinylimidazole ccontent=2.858 meq./g, water content=1.23 meq./g from which can be calculated that $x=17.9$ mole % or 52.1 wt %, $y=35.5$ mole % or 27.5 wt %, $z=46.6$ mole % or 20.4 wt %.

For use of the copolymer in an image-receiving layer the ethanol was removed from this solution while simultaneously adding the same amount of water. Yield: 2486 g, 35 wt %, pH=7. Viscosity of a 20 wt % solution in water at 25° C.: 36.2 mPa s.

PREPARATION 4

In an analogous way as described in preparation 3, an acrylonitrile/N-vinylimidazole/m,p-vinylbenzyl,-tributylphosphonium chloride copolymer was prepared starting with 30 mole % acrylonitrile, 30 mole % vinylimidazole and 40 mole % m,p-vinylbenzyl,-tributylphosphonium choride.

Yield: 905.6 g.

Analysis of the copolymer: phosphonium chloride content=2.073 meq./g, N-vinylimidazole content=1.544 meq./g, water content=2.22 meq./g from which can be calculated that $x=40.45$ mole % or 76.56 wt %, $y=30.1$ mole % or 15.11 wt%, $z=29.45$ mole % or 8.33 wt %.

Viscosity of a 20 wt % solution in water at 25° C: 36.5 mPa s.

A wide variety of acid dyes can be mordanted with the mordanting polymers of the present invention. Such dyes comprise acid groups e.g. carboxylic, sulfonic, ionizable sulfonamide- and hydroxy-substituted aromatic or heterocyclic groups that lend negative charges to the dyes. Such anionic dyes can be readily immobilized by means of the cationic mordanting polymers of the present invention.

Dye images bound by the mordants of this invention exhibit high light stability due to the copolymerized singlet oxygen quenchers that substantially inhibit or retard the fading of the dyes.

In addition the dye-holding properties of the mordants according to the invention can be increased by incorporating hydrophobic monomer units in the phosphonium polymer leading to higher color densities and image sharpness.

A good balance between light-stability and dye-holding properties is obtained when x ranges from about 15 to about 50 mole %, y from about 25 to about 60 mole % and z from about 25 to about 60 mole %.

The present invention also provides an image-receptor element suitable for use in dye diffusion transfer imaging processes which comprises a support and an image-receiving layer incorporating a hydrophilic colloid and a phosphonium mordanting polymer comprising recurring units corresponding to the general formula (I) that is capable of fixing acid dyes transferred to said image-receiving layer by diffusion.

The hydrophilic colloid used as a binder may be any natural or synthetic hydrophilic colloid generally used in the field of photography, such as gelatin, albumin, polyvinyl alcohol, polyvinylpyrrolidone, etc.

The phosphonium mordants according to the present invention may be used in the image-receptor element as a solution of the copolymer mordant in water or as a water-dispersible copolymer latex mordant.

A mixing ratio of the mordanting polymer to the binder and the coverage of the mordanting polymer can easily be determined by those skilled in the art depending on the amount of dye(s) to be mordanted, on the nature of the specific mordanting polymer, on the image-forming process to be used, etc. In general, the ratio of the mordanting polymer to the binder ranges from 20 to about 80% by weight. The mordanting polymer is usually incorporated into the image-receiving layer in amounts varying from about 0.2 to about 15 per $m^2$, preferably from about 0.5 to about 5 g per $m^2$.

The image-receiving layer may also contain other conventional ingredients such as ultraviolet-absorbing substances to protect the mordanted dye images from fading e.g. substituted 2-hydroxyphenyl benzotriazoles and hydroxybenzophenones, brightening agents e.g. stilbenes, coumarins, triazines, oxazoles, or dye stabilizers e.g. butylated hydroxytoluene, substituted chromanols, alkylphenols, plasticizers, surface-active agents, hardeners, etc.

Good results are obtained e.g. when the image-receiving layer, which preferably is permeable to alkaline solution, has a thickness of approximately 2 to 10 um. Of course, the thickness can be modified depending upon the results aimed at.

Two or more kinds of the mordants of this invention may be used in one layer or in two or more layers of the same image-receptor element or mordants of this invention may be used together with other mordants.

The image-receiving layer can be covered with a protective layer, preferably a gelatin protective layer. Neutralizing layers and timing or inert spacer layers can also be employed in the practice of this invention.

The image-receiving layer can be coated directly onto the support or onto an adhesive layer or other layer previously applied to the support.

The support can be any of the transparent or opaque support materials customarily employed in the art. They include paper or paper coated on one or both sides with an Alpha-olefin polymer e.g. polyethylene, glass, and film materials such as e.g. cellulose acetate film, polyvinyl acetal film, polystyrene film, polyethylene terephthalate film, etc.

In one embodiment of this invention, a photosensitive element having one or plural silver halide emulsion layers on a support is, after imagewise exposure, superposed on an image-receptor element having at least one mordanting layer comprising the polymer mordant of this invention on a support in a face-to-face relationship and then processed by spreading an alkaline processing composition between both elements. In this case, the image-receptor element may be peeled off from the photosensitive element.

In another embodiment of this invention, the support, the image-receptor element and the photosensitive element are in an integrated form as is known in the art.

For photosensitive elements in this invention, silver halides and dye image-providing compounds associated with the silver halides are used. The dye image-providing compounds used in this case may be dye image-providing compounds which are initially mobile and become imagewise immobilized when the photosensitive element is processed by the alkaline processing composition, or initially immobile and become imagewise mobilized during processing.

The mordants used in accordance with the present invention can also be employed in hydrophilic colloid layers of a photographic silver halide element to mordant e.g. antihalation or filter dyes.

The present invention is illustrated by the following examples.

EXAMPLE 1

Preparation of a Phosphonium Homopolymer (a) Preparation of poly(m,p-chloromethylstyrene)

In a closed mixing vessel at room temperature a homogeneous solution was prepared consisting of 610.0 g (4.0 mole) of m,p-chloromethylstyrene, 3.05 g of azobisisobutyronitrile and 451 ml of butanon.

In a 2-liter reactor vessel provided with a nitrogen inlet, stirrer, reflux condenser and thermometer 500 ml of this solution was introduced. The solution was heated under nitrogen atmosphere to 80° C. while stirring. This temperature was reached after 45 minutes. The polymerization reaction proceeded exothermally and the heating was turned off. The temperature of the liquid droped to 75° C.

After 1 h 25 min the heating was turned on again and one started to pump over the rest of the monomer solution out off the mixing vessel at a rate of 8-9 ml/min. The heating was tuned to a temperature variation of 79°-80° C. After 2 h 10 min the monomer solution had been completely pomped into the reaction vessel.

After a reaction period of 7 hours 3.05 g of azobisisobutyronitrile was added and this was repeated after 23 hours.

After a total reaction time of 29 hours the polymer solution in the reaction vessel was cooled, diluted with 300 ml of ethanol and run with a fine jet into a mixture of 2.25 l of ethanol and 2.25 l of n-hexane while stirring efficiently.

The precipitated polymer was dried at 50° C. under vacuum (ca. 1 mm Hg) till constant weight.

Yield: 606 g.

Analysis of chlorine: 22.72%.

(b) Preparation of a phosphonium homopolymer

In a 3-liter rector vessel provided with stirrer, reflux condenser and thermometer, 604.7 g (3.965 mole) of the poly(m,p-chloromethylstyrene) of the previous step were dissolved in dimethylformamide to obtain a total volume of 2025 ml. This solution was gradually heated while stirring.

After 10 minutes the temperature had raised to 45° C. and 843.16 g (3.965 mole) of 95% tributylphosphine were added at a rate of 8.5-9 g/min.

After 30 minutes the temperature in the solution yielded 74° C. and the heating was slowed down because of the slightly exothermic reaction. After 50 minutes the solution in the reaction vessel was at 80° C. and during the further reaction periode the heating was tuned so as to keep the temperature between 79° C. and 81° C.

After a reaction period of 6 hours the reaction was stopped and the polymer solution was cooled to room temperature.

By slowly pouring out the solution in a mixture of 5 l of hexane and 5 l of ether while stirring, the phosphonium polymer was isolated as a viscous mass. After decantating the supernatant and washing in 8 l of ethylacetate the polymer was filtered off and finally dissolved in water from which the residual dissolved ethylacetate was removed by partial distillation.

Yield: 4000 g of solution, 33.76 wt %.

Analysis of ionic chlorine: 2.688 meq./g.

A polyethylene coated paper support that has a thickness of 170 um and has been subbed with a glelatin layer after corona treatment was coated with an image-receiving layer comprising per m$^2$: gelatin (2.4 g), the phosphonium homopolymer mordant as described above (2.0 g), formaldehyde (0.02 g). In this way comparitive image receptor element 1 for dye diffusion transfer was obtained.

A light-sensitive color diffusion transfer material as described in the example of U.S. Pat. No. 4,496,645 was exposed through a grey wedge having a constant of 0.1 and through a blue, green and red filter, respectively and then each of the three color separation images was developed while in contact with the image-receiving layer of the aliquot portion of the above image-receptor element in a COPYPROOF T 42 diffusion transfer reversal processing apparatus (COPYPROOF is a registered trademark of Agfa-Gevaert N. V., Belgium) containing an aqueous alkaline activating bath comprising per liter: sodium hydoxide (25 g), sodium orthophosphate (25 g), cyclohexane dimethanol (25 g), sodium thiosulfate (2 g), potassium iodide (2 g), 2,2-methylpropylpropane diol (25 g), N-ethylbenzenepyridinium chloride (0.5 g) and distilled water to make 1000 ml.

After a contact time of 2 minutes, the respective receptor elements 1 were separated from the respective light-sensitive materials and rinsed and dried in a COPYPROOF WD 37 rinsing and drying apparatus.

The above described procedure was repeated in exactly the same way with image-receptor elements 2 to 4 comprising instead of the phosphonium homopolymer the above described phosphonium mordanting agents of preparation 1 to 3 respectively (having an equivalent amount of quaternated phosphonium per m$^2$ compared with the phosphonium homopolymer).

The maximum density of the mordanted yellow (Y), magenta (M) and cyan (C) dyes obtained on the different receptor elements was measured in reflection by means of a MACBETH QUANTOLOG color densitometer.

All image receptor elements were also placed in a XENOTEST (trade mark) type 150 apparatus of Hanau Quartzlampen Gmbh, Hanau, W. Germany and exposed therein for 8 hours with a Xenon lamp 150 (180 klux). The maximum density of each color separation image was measured again. The percent loss of density in each color separation image is a standard for the light stability of the mordanted dyes.

The results of the evaluations are listed in table 1.

TABLE 1

| receptor no | mordant prep.no. | maximum density | | | % loss of density | | |
|---|---|---|---|---|---|---|---|
| | | Y | M | C | Y | M | C |
| 1 | homo | 198 | 202 | 205 | 68 | 58 | 49 |
| 2 | 1 | 190 | 190 | 195 | 34 | 31 | 35 |
| 3 | 2 | 188 | 191 | 192 | 35 | 25 | 33 |
| 4 | 3 | 200 | 202 | 205 | 36 | 27 | 35 |

These results show that the light stability of the mordanted dyes is strongly increased by incorporating N-vinylimidazole in the phosphonium polymer.

EXAMPLE 2

The bleeding (diffusing) tendency of the dyes mordanted with image receptor element 3 and 4 was checked visually. In image receptor element 4 the mordanted dyes were more firmly hold and did not migrate; sharper images than in image receptor element 3 were obtained.

These results show that by incorporating besides N-vinylimidazole acrylonitrile in the phosphonium polymer the dye-holding properties of the mordant are increased.

We claim:

1. Photographic element having on a support at least one layer containing a phosphonium mordanting polymer comprising randomly distributed recurring units corresponding to the general formula (I)

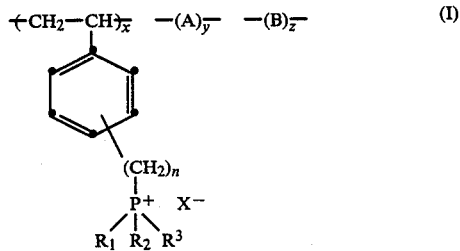

wherein:
A represents a unit that is derived from a copolymerizable ethylenically unsaturated monomer capable of quenching singlet oxygen;
B represents a unit that is derived from a copolymerizable ethylenically unsaturated monomer having a hydrophobic character;
n represents an integer of from 1 to about 12;
each of $R_1$, $R_2$ and $R_3$ (same or different) represents a $C_1$-$C_8$ alkyl group, a cycloalkyl group or an aryl group;
$X^-$ represents an acid anion;
x represents from about 5 mole % to about 80 mole %;
y represents from about 20 mole % to about 95 mole % and
z represents from 0 mole % to about 65 mole %.

2. Photographic element according to claim 1, wherein A is N-vinylimidazole or 2-methyl-1-vinylimidazole.

3. Photographic element according to claim 1, wherein B is acrylonitrile or methacrylonitrile.

4. Photographic element according to claim 1, wherein A is N-vinylimidazole or 2-methyl-1-vinylimidazole and wherein B is acrylonitrile or methacrylonitrile.

5. Photographic element according to claim 4, wherein n equals 1.

6. Photographic element according to claim 4, wherein $R_1$, $R_2$ and $R_3$ each represent an alkyl group.

7. Photographic element according to claim 4, wherein $X^-$ is a halogen ion.

8. Photographic element according to claim 4, wherein n equals 1 and wherein $R_1$, $R_2$ an $R_3$ each represent an alkyl group and wherein $X^-$ is a halogen ion.

9. Photographic element according to claim 1, wherein said mordanting polymer is used as a solution in water and wherein x ranges from about 15 to about 50 mole %, y ranges from about 25 to about 60 mole % and z ranges from about 25 to about 60 mole %.

10. Photographic element according to claim 1 which is an image-receptor element suitable for use in dye diffusion transfer imaging processes.

11. Photographic element according to claim 10 wherein said image-receptor element is in an integrated form with a photosensitive element comprising at least one light-sensitive silver halide emulsion layer and associated with said silver halide emulsion layer a dye-providing substance.

12. Phosphonium mordanting polymer, that is capable of fixing acid dyes and that comprises randomly distributed recurring units corresponding to the general formula (I)

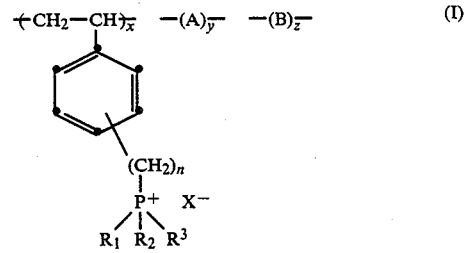

wherein:
A represents a unit that is derived from a copolymerizable ethylenically unsaturated monomer capable of quenching singlet oxygen;
B represents a unit that is derived from a copolymerizable ethylenically unsaturated monomer having a hydrophobic character;
n represents an integer of from 1 to about 12;
each of $R_1$, $R_2$ and $R_3$ (same or different) represents a $C_1$-$C_8$ alkyl group, a cycloalkyl group or an aryl group;
$X^-$ represents an acid anion;
x represents from about 5 mole % to about 80 mole %;
y represents from about 20 mole % to about 95 mole % and
z represents from 0 mole % to about 65 mole %.

* * * * *